United States Patent [19]

Pamer et al.

[11] Patent Number: 4,532,338
[45] Date of Patent: Jul. 30, 1985

[54] PROCESS FOR PRODUCING 2-HALOMETHYL-1,3-CYCLIC ACETAL

[75] Inventors: Steven E. Pamer, Norton; James A. Cook, Jr., Barberton, both of Ohio

[73] Assignee: PPG Industries, Inc., Pittsburgh, Pa.

[21] Appl. No.: 513,478

[22] Filed: Jul. 13, 1983

[51] Int. Cl.$^3$ .................. C07D 317/00; C07D 319/06
[52] U.S. Cl. ..................................... 549/455; 549/369
[58] Field of Search ................................ 549/455, 369

[56] References Cited

U.S. PATENT DOCUMENTS

| | | | |
|---|---|---|---|
| 2,330,570 | 9/1943 | Filachione | 260/615 |
| 2,411,826 | 11/1946 | Filachione | 260/615 |
| 3,431,281 | 3/1969 | Sawaya | 260/340.9 |
| 4,110,101 | 8/1978 | Stach et al. | 71/88 |
| 4,113,464 | 9/1978 | Stach et al. | 71/88 |
| 4,116,670 | 9/1978 | Stach et al. | 71/88 |
| 4,294,764 | 10/1981 | Rinehart | 260/340.9 R |

FOREIGN PATENT DOCUMENTS 739022 10/1955 United Kingdom .

OTHER PUBLICATIONS

J.A.C.S., vol. 61, pp. 1705–1706, Jul. 1939.
J.A.C.S., vol. 70, pp. 3781–3786 (1948).

*Primary Examiner*—Ethel G. Love
*Attorney, Agent, or Firm*—Irwin M. Stein

[57] ABSTRACT

The yield and purity of 2-halomethyl-1,3-cyclic acetals is improved by subjecting the reaction product of 1,2-dihaloethyl acetate and aliphatic diol to alkaline hydrolysis. The resulting aqueous and organic phases are separated and the organic phase distilled to recover the 2-halomethyl-1,3-cyclic acetal product.

19 Claims, No Drawings

PROCESS FOR PRODUCING 2-HALOMETHYL-1,3-CYCLIC ACETAL

DESCRIPTION OF THE INVENTION

The present invention relates to an improved process for the preparation of 2-halomethyl-1,3-cyclic acetals which can be used as intermediates for the preparation of substituted amides. U.S. Pat. Nos. 4,110,101, 4,113,464, and 4,116,670 describe dioxepane-, dioxolan-, and dioxane-substituted amides which are reported to be useful as herbicides, e.g., preemergence grass herbicides. U.S. Pat. No. 4,294,764 describes dioxolan- or dioxane-2-ylmethyl substituted 2,2-dichloroacetamides as antidotes to protect crops from the phytotoxic effect of active thiolcarbamate herbicides, such as ethyl di-n-propyl thiolcarbamate (EPTC).

The aforesaid patents describe synthesizing said acetamides by a route which includes the reaction of a cyclic acetal, such as a 2-halomethyl-1,3-cyclic acetal, e.g., 2-chloromethyl-1,3-dioxolane, with a substituted amine. See, for example, column 5, lines 28-59 of U.S. Pat. No. 4,294,764. The cyclic acetals can be prepared by reacting the corresponding acyclic acetal with a lower aliphatic diol, e.g., ethylene glycol.

The synthesis of acetals of halogenated aldehydes, such as chloro-. acetaldehyde and bromoacetaldehyde, by various methods has been reported. One such method involves the halogenation of a vinyl-type ester followed by treatment of the halogenated product with a suitable alcohol. For example, vinyl acetate can be chlorinated in the presence of an aliphatic alcohol, such as ethyl or methyl alcohol, to produce the corresponding acetal of chloroacetaldehyde. The alcohol may be present during the halogenation step, or it can be added to the halogenated vinyl ester as a second separate step. See, for example, "A New Synthesis of Acetals of Chloroacetaldehyde and Bromoacetaldehyde" by Edward M. Filachione, J.A.C.S., Vol. 61, pages 1705-06, July 1939, and U.S. Pat. No. 2,330,570. More complex acetals, e.g., cyclic acetals, can be prepared by using polyhydric alcohols, such as ethylene glycol, propylene glycol, etc., as the alcohol. See U.S. Pat. No. 2,411,826.

In the aforedescribed method for preparing cyclic acetals, the yield of the cyclic acetal, based on the starting reactant vinyl acetate, has not been highly satisfactory. Moreover, we have found that the cyclic acetal product contains by-products which are not readily separable by simple distillation. Such by-products interfere with the effective utilization of the cyclic acetal as an intermediate in the preparation of other biochemically active materials by reducing the yield of the desired biochemically active material and/or by introducing undesired impurities therein.

It has now been discovered that the aforesaid yield and purity of cyclic acetals, particularly 2-halomethyl-1,3-cyclic acetals, can be substantially improved by subjecting the aliphatic diol halogenated vinyl acetate reaction product mixture to alkaline hydrolysis. In particular, an aqueous alkaline reagent, such as aqueous sodium hydroxide, is added to the aforesaid reaction mixture in amounts sufficient to substantially hydrolyze the hydrolyzable acyclic ester by-products in the reaction mixture. The hydrolyzed by-products are found in the resulting aqueous phase and are easily separated from the organic phase containing the cyclic acetal. Topping of the resulting organic phase to remove readily volatile components produces a cyclic acetal product of improved purity and yield.

U.S. Pat. No. 2,411,826 describes adding a potassium carbonate solution to a reaction mixture formed by admixing ethylene glycol with chlorinated vinyl acetate to make the mixture alkaline (column 3, line 73—column 4, line 14). Use of the potassium carbonate solution in the aforedescribed example is to neutralize the hydrogen halide formed in the alcohol exchange reaction. Alkaline hydrolysis differs from neutralization of hydrogen halide with potassium carbonate by (1) the presence of a more strongly nucleophilic group, i.e., $OH^-$, by (2) the longer time required to accomplish the hydrolysis step, and (3) by the preferred application of heat to accelerate the desired hydrolysis reaction.

DETAILED DESCRIPTION

In the process for preparing 2-halomethyl-1,3-cyclic acetals described herein, vinyl acetate is halogenated to produce a first reaction mixture containing 1,2-dihaloethyl acetate. The halogen used for the halogenation reaction is selected from the group consisting of chlorine and bromine. The first reaction mixture containing the 1,2-dihaloethyl acetate is reacted with a lower aliphatic diol, e.g., a $C_2$-$C_4$ alkylene diol, by admixing the diol with the first reaction mixture, thereby to produce a second reaction mixture containing the 2-halomethyl-1,3-cyclic acetal and acyclic ester by-products.

In a preferred embodiment, the second reaction mixture is heated to accelerate and complete the alcohol exchange reaction. More preferably, the heating step includes removing by-product water by azeotropic drying of the second reaction mixture.

In accordance with the process of the present invention, the second reaction mixture, e.g., the dried reaction mixture, is admixed with aqueous alkaline reagent in an amount and for a time sufficient to substantially hydrolyze the hydrolyzable acyclic ester by-products in the second reaction mixture. The resulting aqueous phase and organic phase are separated and the organic phase is heated to remove the readily volatile components within the organic phase.

Alkaline reagents which can be used to provide the aqueous alkaline solutions used for the alkaline hydrolysis step of the present invention are those which provide the strong nucleophilic group, $OH^-$, (other than water), and principally include the readily available aqueous solutions of alkali metal hydroxides, e.g., sodium hydroxide and potassium hydroxide. The concentration of the alkali metal hydroxide used can vary, but typically will be between about 5 and 35, e.g., between 10 and about 30 weight percent. A 20 weight percent aqueous sodium hydroxide solution has been found to be suitable for conducting the hydrolysis step.

The time required for the alkaline hydrolysis will vary with the concentration of the alkaline reagent and the temperature used. Generally, such time will be that required to substantially hydrolyze the acyclic ester by-products found in the aforesaid second reaction mixture. Such time can vary from about 0.5 or 2 to about 20 hours depending on the aforesaid conditions of hydrolysis and is significantly longer than the time required to neutralize the hydrogen halide formed in the alcohol exchange reaction. Experience to date indicates that hydrolysis is substantially complete after stirring the mixture of aqueous alkaline reagent and second reaction for from about 0.5 to 20 hours at ambient temperatures or after about 2 to 4 hours while refluxing the aforesaid mixture at temperatures of from about 50°C.–90° C. Alkaline hydrolysis has been found to reduce the concentration of the hydrolyzable cyclic ester by-products to below about 1% by weight of the 2-halomethyl-1,3-cyclic acetal product without adversely affecting the cyclic acetal product.

The amount of alkaline reagent used to effect the hydrolysis can vary. Generally, the molar ratio of alkali metal hydroxide, e.g., sodium hydroxide, to the halogenated vinyl acetate, i.e., 1,2-dihaloethyl acetate, will vary from about 1.7:1 to about 2.3:1. Alternatively, the amount of alkali metal hydroxide used can be expressed as from 1.7 to 17 equivalents of such hydroxide based on the amount of vinyl acetate halogenated. The temperature at which hydrolysis is performed can also vary. Typically, temperatures of from about ambient temperature, e.g., about 20° C., to about 90° C. are suitable.

In addition to the 2-halomethyl-1,3-cyclic acetal, the second reaction mixture contains acyclic ester and non-ester by-products, such as the aliphatic diol used, e.g., ethylene glycol, haloacetaldehyde, such as chloroacetaldehyde ($ClCH_2CHO$), haloethanol, e.g., 2-chloroethanol ($ClCH_2CH_2OH$), acetic acid ($CH_3COOH$), haloethylesters of acetic acid, such as 2-chloroethyl acetate ($ClCH_2CH_2O(O)CCH_3$), hydroxyalkyl esters of acetic acid, such as 2-hydroxyethyl acetate ($HOCH_2CH_2O(O)CCH_3$), and alkylene diacetate, such as ethylene diacetate ($CH_3C(O)OCH_2CH_2O(O)CCH_3$). Further, if an inert organic solvent is used in the vinyl acetate halogenation reaction, or if an organic solvent is added to the aliphatic diol-1,2-dihaloethyl acetate exchange reaction, such solvent(s) will also be present in the second reaction mixture.

Certain of the by-products present in the second reaction mixture are difficult to separate from the cyclic acetal product. For example, 2-chloroethyl acetate and 2-hydroxyethyl acetate have boiling points sufficiently close to 2-chloromethyl-1,3-dioxolane to prevent separation of the by-products by simple distillation. It now appears from the evidence at hand that when the second reaction mixture is subjected to aqueous alkaline hydrolysis, acyclic ester by-products found therein are hydrolyzed to acetic acid, water and the corresponding aliphatic diol, i.e., alkylene diol such as ethylene glycol, which are removed with the resulting aqueous phase. Surprisingly, the cyclic acetal product appears to remain unaffected during the alkaline hydrolysis step.

In a preferred embodiment of the present invention, an inert organic solvent which forms an azeotrope with water at less than 85° C. is added to the second reaction mixture. The solvent should also be stable under acidic and alkaline conditions. The addition of the inert organic solvent to the second reaction mixture permits the removal of water therefrom by azeotropic distillation, and further serves to enhance the separation of the organic components of the reaction mixture from the aqueous phase formed by the addition of the aqueous alkaline reagent thereto.

Examples of suitable inert organic solvents which can be added to the second reaction mixture include benzene, cyclohexane, ethylene dichloride, pentane, and hexane. Preferably, the organic solvent-water azeotrope boils at no greater than about 82° C. for the reason that chloroacetaldehyde has a boiling point of about 87° C.

The amount of inert organic solvent added to the second reaction mixture can vary widely, e.g., the ratio of volumes of organic solvent to second reaction mixture can vary from 0.1:1 to 20:1. More typically, the ratio of volumes will vary from 0.5:1–5:1, e.g., 1:1. The inert organic solvent is used in amounts sufficient to promote ease of separation between the later formed organic and aqueous phases and to form an azeotrope with substantially all of the water formed in the second reaction mixture.

As previously indicated, the halogenation of vinyl acetate can be conducted in the presence of an inert organic solvent, i.e., one which does not halogenate under the conditions of halogenation. If the halogenation reaction is performed in the presence of such an organic solvent, it is preferred that the organic solvent be one which forms an azeotrope with water at leas than 85° C. so that the solvent used in the halogenation reaction and in the aliphatic diol-1,2-dihaloethyl acetate exchange reaction can be the same.

Alternatively, the water present in the second reaction mixture can be removed by contacting the mixture with an inorganic drying reagent such as magnesium sulfate, calcium chloride, sodium sulfate and the like or by the use of an ion exchange resin. The water-lean second reaction mixture is then contacted with the aqueous alkaline reagent to hydrolyze acyclic ester by-products.

Following alkaline hydrolysis of the second reaction mixture, the resulting aqueous and organic phases are separated by conventional methods. The aqueous phase can be washed with the same inert organic solvent added to the second reaction mixture so as to extract any organic components separated with the aqueous phase. The volumetric ratio of solvent to aqueous phase can vary but generally will be in the range of 0.1:1 to 1:1. The resulting mixture is permitted to phase separate and this further organic phase separated and combined with the original organic phase.

The organic phase (or the combined organic phases) containing the cyclic acetal is heated to remove the readily volatile components of the organic phase. Typically, the organic phase is heated to temperatures sufficient to remove the inert organic solvent and other organic components which are more volatile than the cyclic acetal product. This topping or distillation of the organic phase can be performed by known conventional techniques. The process of the present invention produces a cyclic acetal having a purity of at least 88 percent, more usually at least 94 percent.

The 2-halomethyl-1,3-cyclic acetals to which the improved process of the present invention is directed can be represented by the following graphic formula:

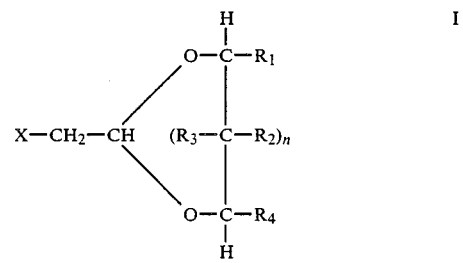

I wherein X is halogen, e.g., chlorine or bromine, $R_1$, $R_2$, $R_3$, and $R_4$ are hydrogen or methyl and n is an integer from 0 to 2. When n is 2, each of the $R_2$ and $R_3$ groups attached to its respective methylene group is independently hydrogen or methyl. Preferably, n is zero (0) or 1 and $R_1$, $R_2$, $R_3$ and $R_4$ are hydrogen. Examples of 2-halomethyl-1,3-cyclic acetals include the following:
2-chloromethyl-1,3-dioxolane
2-chloromethyl-4-methyl-1,3-dioxolane
2-chloromethyl-4,5-dimethyl-1,3-dioxolane
2-chloromethyl-1,3-dioxane
2-chloromethyl-4-methyl-1,3-dioxane
2-chloromethyl-5-methyl-1,3-dioxane
2-chloromethyl-5,5-dimethyl-1,3-dioxane
2-chloromethyl-4,5-dimethyl-1,3-dioxane
2-chloromethyl-4,5,5 trimethyl-1,3-dioxane
2-chloromethyl-4,5,5,6-tetramethyl-1,3-dioxane
2-chloromethyl-4,6-dimethyl-1,3-dioxane
2-chloromethyl-4,5,6-trimethyl-1,3-dioxane
2-chloromethyl-4-methyl-1,3-dioxepane
2-chloromethyl-4,5-dimethyl-1,3-dioxepane
2-chloromethyl-4,5,5-trimethyl-1,3-dioxepane
2-chloromethyl-4,5,5,6-tetramethyl-1,3-dioxepane
2-chloromethyl-4,5,5,7-tetramethyl-1,3-dioxepane
2-chloromethyl-4,5,5,6,6-pentamethyl-1,3-dioxepane
2-chloromethyl-4,5,5,6,6,7-hexamethyl-1,3-dioxepane
2-chloromethyl-4,6-dimethyl-1,3-dioxepane
2-chloromethyl-4,5,6-trimethyl-1,3-dioxepane
2-chloromethyl-4,6,6-trimethyl-1,3-dioxepane
2-chloromethyl-4,7-dimethyl-1,3-dioxepane
2-chloromethyl-5,6-dimethyl-1,3-dioxepane
2-chloromethyl-5-methyl-1,3-dioxepane
2-chloromethyl-5,5-dimethyl-1,3-dioxepane
2-chloromethyl-4,5,7-trimethyl-1,3-dioxepane
2-chloromethyl-5,5,6-trimethyl-1,3-dioxepane
2-chloromethyl-4,5,6,7-tetramethyl-1,3-dioxepane
2-chloromethyl-4,5,6,6-tetramethyl-1,3-dioxepane
2-chloromethyl-4,5,5,6,7-pentamethyl-1,3-dioxepane
2-chloromethyl-1,3-dioxepane.

In the above compounds, the chlorine substituent in the chloromethyl group can be replaced with bromine and similar results expected.

The above-described cyclic acetals are produced by halogenation of vinyl acetate to produce 1,2-dihaloethyl acetate which, in turn, is admixed with a lower aliphatic diol to produce the corresponding cyclic acetal. The aliphatic diols used to produce the above-described cyclic acetals can be represented by the following graphic formula:

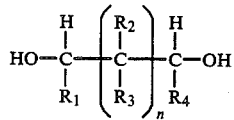

II wherein $R_1$, $R_2$, $R_3$, $R_4$ and n are as defined above with respect to graphic formula I. Examples of such aliphatic diols are ethylene glycol, propylene glycol and 1,4-butane diol.

In the halogenation reaction, vinyl acetate is halogenated with a halogen selected from the group consisting of chlorine and bromine, preferably chlorine. The halogenation can be conducted at room temperature or above, but in order to improve the yield of the 1,2-dihaloethyl acetate it has been found desirable to avoid the use of temperatures which are unnecessarily high. In most cases, it has been found that the yield of the 1,2-dihaloethyl acetate is improved by conducting the halogenation at comparatively low temperatures, generally below 10° C., e.g., between about 0° and 5° C.

If desired, an inert organic solvent, which can conveniently be separated by distillation from the cyclic acetal to be produced, can be used as the medium in which the halogenation reaction is conducted. The inert solvent should be resistant to halogenation at the conditions of the halogenation reaction and, as described, have a boiling point substantially below the boiling point of the cyclic acetal to allow a convenient separation from the acetal by topping or distillation. Further, it is preferred that the inert organic solvent used in the halogenation reaction form an azeotrope with water, which azeotrope boils at less than about 85° C. Examples of an organic solvent that can be used for the halogenation reaction are benzene, pentane and hexane, preferably benzene.

The amount of halogen used in the halogenation reaction is at least in stoichiometric amounts, i.e., at least one mole of diatomic halogen for every mole of vinyl acetate. Typically, the amount of halogen used will be slightly in excess of the stoichiometric amounts required to insure that all of the vinyl acetate charged to the halogenation vessel is halogenated. A large excess of chlorine, e.g., greater than 10 mole percent, is to be avoided.

The first reaction mixture comprising the 1,2-dihaloethyl acetate, e.g., 1,2-dichloroethyl acetate, is admixed with the aliphatic diol of graphic formula II to form a second reaction mixture containing 2-halomethyl-1,3-cyclic acetal. The amount of aliphatic diol used can vary but should be in at least stoichiometric amounts with respect to the amount of 1,2-dihaloethyl acetate in the first reaction mixture. More typically, the aliphatic diol is added to the first reaction mixture in a mole ratio, based on the amount of vinyl acetate charged to the halogenation reactor, of at least 2:1, e.g., from about 2:1 to about 5:1. The aliphatic diol/1,2-dihaloethyl acetate exchange reaction forms the corresponding 2-halomethyl-1,3-cyclic acetal.

The temperature at which the aforesaid reaction is conducted can vary. Typically, the second reaction mixture is permitted to warm to ambient temperature from the relatively cool halogenation temperatures heretofore described. The by-product hydrogen halide formed by the aforesaid exchange reaction also serves to catalyze the reaction. The length of time required for completion of the exchange reaction will vary indirectly with the temperature, and may range from 0.5 to 72, e.g., 0.5 to 16, hours. Preferably, the organic solvent is added to the second reaction mixture (if not already present) and the water present therein removed by azeotropic distillation, during which the exchange reaction is substantially completed.

In accordance with a preferred embodiment of the present invention, vinyl acetate is chlorinated at about 0°–5° C. to produce a first reaction mixture containing 1,2-dichloroethyl acetate. Ethylene glycol is admixed with the first reaction mixture and allowed to warm to room temperature thereby to form a second reaction mixture containing 2-chloromethyl-1,3-dioxolane and acyclic ester by-products including 2-chloroethyl acetate. Benzene is added to the second reaction mixture and the resulting mixture heated to above the boiling point of the benzene-water azeotrope, i.e., about 70° C., to remove same. Following removal of the benzene-water azeotrope, an aqueous solution of sodium hydroxide is added to the resulting water-lean mixture and this mixture stirred for about 2 hours at about 50° C. The aqueous and organic phases are permitted to separate and the aqueous phase separated from the organic phase containing the 2-chloromethyl-1,3-dioxolane. The separated organic phase is distilled to remove the remaining benzene solvent and other volatile organic compounds having a boiling point less than about 85° C., thereby to produce 2-chloromethyl-1,3-dioxolane of improved purity.

The process of the present invention is more particularly described in the following Examples which are intended as illustrative only since numerous modifications and variations therein will be apparent to those skilled in the art. Unless otherwise specified in the Examples, temperatures are in degrees centigrade and parts, percentages, and proportions are by weight. Analysis of the aqueous and organic phases is by gas chromatography (GC) and the relative concentrations of the components of such phases are reported in peak area percents.

EXAMPLE 1

A jacketed four liter flask equipped with a bottom outlet and four Teflon baffles to increase mixing was used as a chlorination vessel. The vessel was purged with nitrogen and then charged with 8.0 moles (688.7 grams) of vinyl acetate and 1160 milliliters of benzene. The resulting mixture was stirred rapidly with a turbine type Teflon agitator attached to a Teflon coated steel shaft. A refrigerated coolant was circulated through the jacket of the vessel to control the temperature of the contents of the vessel, which were cooled to less than −10° C. Chlorine gas (583 grams, 8.22 moles) was slowly added over 1½ hours beneath the surface of the liquid mixture near the agitator through a fritted gas dispersion tube. The liquid mixture was protected from the light during chlorination by wrapping the vessel with aluminum foil. The temperature of the solution during chlorination was about from −1° C. to +4° C. The chlorine remaining in the tubing and safety trap after the addition of chlorine was completed was purged with a stream of nitrogen, thereby transferring the chlorine into the reaction mixture.

The cold chlorinated solution was added to 40.16 moles (2492.6 grams) of ethylene glycol. A slight exothermic reaction was observed and the temperature of the mixture rose to about 56° C. The resulting reaction mixture was stirred rapidly for about 3 hours. A sample of the reaction mixture was taken at the end of this 3 hours and the phases were allowed to separate. Both phases were analyzed by gas chromatography (GC). The relative amounts of the components of both phases, as estimated by peak area percent, are reported in Table I.

TABLE I

| | Peak Area % | |
|---|---|---|
| Component | Lower Phase | Upper Phase |
| Water | 8.9 | 0.2 |
| Chloroacetaldehyde | 0.7 | 0.7 |
| Benzene | 3.0 | 47.2 |
| 2-Chloroethanol | 3.9 | 1.6 |
| Ethylene Glycol | 57.4 | 1.9 |
| 2-Chloroethyl Acetate | 4.8 | 2.3 |
| 2-Hydroxyethyl Acetate | 12.6 | 7.1 |
| 2-Chloromethyl-1,3-Dioxolane | 6.8 | 33.8 |
| Others | Remainder | Remainder |

EXAMPLE 2

An aliquot (aliquot A, 1753 grams, 36.8% of the total) of the reaction mixture produced in Example 1 was separated from the total and refluxed in a Dean-Stark apparatus overnight (about 16 hours) to complete the reaction and remove water as a benzene-water azeotrope. The remaining portion of the reaction mixture (about 3012) grams, 63.2% of the total) was stirred overnight (about 16 hours) at room temperature (about 22° C.). About 192 grams of distilled azeotrope were recovered and permitted to phase separate. Both phases were analyzed by GC. The aqueous phase (about 125 grams) was about 90 percent water, 5 percent 2-chloroethanol and 3 percent ethylene glycol. The organic phase was about 95 percent benzene, 2 percent 2-chloroethanol and 1 percent 2-chloromethyl-1,3-dioxolane.

The undistilled residue was distilled in a 1 inch×12 inch glass helice-packed distillation column and distillate fractions recovered over various increasing temperature increments. Each of the recovered fractions was analyzed by GC analysis.

At a head temperature range of from about 78.5° C.–80.8°, the distillate fractions collected were principally benzene, i.e., 97.7–99+ percent benzene. At a head temperature of from about 81° C. to 117° C., the distillate fraction comprised about 81 percent benzene, 12 percent 2-chloroethanol, 1.7 percent 2-hydroxyethyl acetate, 1 percent water and 1.7 percent 2-chloromethyl-1,3-dioxolane.

At a head temperature of from 122.5°–130° C., the distillate comprised about 5 percent water, about 1 percent chloroacetaldehyde, 68 percent 2-chloroethanol, 11 percent 2-chloroethyl acetate, and 14 percent 2-chloromethyl-1,3-dioxolane. At a head temperature of from about 131°–143° C., the distillate comprised about 4 percent water, 1 percent chloroacetaldehyde, 43 percent 2-chloroethanol, 1 percent ethylene glycol, 18 percent 2-chloroethyl acetate, and 33 percent 2-chloromethyl-1,3-dioxolane.

The fractions of the distillate recovered over a head temperature range of 145° C.–175° C. were combined and phase separated. Each of the phases was analyzed by GC and the results are reported in Table II.

TABLE II

| | Peak Area % | |
|---|---|---|
| Component | Lower Phase | Upper Phase |
| Water | 1.5 | 29.2 |
| Chloroacetaldehyde | 0.4 | 1.6 |
| 2-Chloroethanol | 5.0 | 5.8 |
| Ethylene Glycol | 2.3 | 48.1 |
| 2-Chloroethyl Acetate | 8.9 | 0.9 |
| 2-Hydroxyethyl Acetate | 1.0 | 2.3 |
| 2-Chloromethyl-1,3-Dioxolane | 79.7 | 11.7 |
| Others | Remainder | Remainder |

EXAMPLE 3

The remaining portion of the reaction mixture produced in Example 1 was phase separated and analyzed by GC. Results are tabulated in Table III.

TABLE III

| | Peak Area % | |
|---|---|---|
| Component | Lower Phase | Upper Phase |
| Water | 10.8 | 0.4 |
| Chloroacetaldehyde | 1.3 | 0.3 |
| Benzene | 5.7 | 49.5 |
| 2-Chloroethanol | 5.6 | 2.3 |
| Ethylene Glycol | 47.3 | 1.7 |
| 2-Chloroethyl Acetate | 3.1 | 2.1 |
| 2-Hydroxyethyl Acetate | 16.1 | 6.5 |
| 2-Chloromethyl-1,3-Dioxolane | 8.8 | 31.9 |

TABLE III-continued

| Component | Peak Area % | |
|---|---|---|
| | Lower Phase | Upper Phase |
| Others | Remainder | Remainder |

A second aliquot (aliquot B, of 1218.9 grams) of this reaction mixture was refluxed overnight in a Dean-Stark apparatus at a head temperature of 73° C. and a pot temperature of 88° C. Due to a leak in the system, most of the benzene solvent was lost. The aqueous phase recovered in the azeotropic distillation and the still pot residue were analyzed by GC. Benzene was added to the still pot residue to dissolve the contents and the resulting solution also analyzed by GC. Results are tabulated in Table IV.

TABLE IV

| | Peak Area % | | |
|---|---|---|---|
| Component | Aqueous Phase | Still Pot Residue | Still Pot Solution |
| Water | 88.2 | 0.8 | — |
| Chloroacetaldehyde | 1.2 | 0.3 | 0.2 |
| Benzene | 0.1 | 0.1 | 31.2 |
| 2-Chloroethanol | 7.7 | 14.8 | 11.3 |
| Ethylene Glycol | 2.2 | 27.0 | 17.4 |
| 2-Chloroethyl Acetate | T | 4.1 | 2.9 |
| 2-Hydroxyethyl Acetate | 0.1 | 18.6 | 12.5 |
| 2-Chloromethyl-1,3-Dioxolane | 0.3 | 28.6 | 19.4 |
| Others | Remainder | Remainder | Remainder |

T = Trace 820 grams of 20 percent aqueous sodium hydroxide was added to the still pot solution and the resulting solution refluxed for about three hours. A sample of the organic phase was taken after 2.5 hours and analyzed by GC. Results are tabulated in Table V. The refluxed solution was cooled and phase separated. The aqueous phase was extracted with about 150 milliliters of benzene, the benzene extract combined with the separated organic phase, and the combined organic phases refluxed in a Dean-Stark apparatus to remove any residual water. The resulting substantially water-free organic phase was distilled in a 1 inch×12 inch glass helice-packed distillation column and three fractions obtained at head temperatures of 80°–81.5° C. (fraction 1), 82°–154° C. (fraction 2), and 154°–157° C. (fraction 3). Each of the fractions was analyzed by GC. Results are tabulated in Table V.

TABLE V

| Component | Refluxed Solution | Distillate Fraction | | |
|---|---|---|---|---|
| | | 1 | 2 | 3 |
| Water | 12.2 | 0.3 | 0.2 | 0.5 |
| Chloroacetaldehyde | 0.3 | — | 0.1 | 0.1 |
| Benzene | 54.8 | 99.5 | 66.8 | — |
| 2-Chloroethanol | — | — | — | — |
| Ethylene Glycol | 3.1 | — | 7.7 | — |
| 2-Chloroethyl Acetate | T | — | — | — |
| 2-Hydroxyethyl Acetate | T | — | — | — |
| 2-Chloromethyl-1,3-Dioxolane | 29.6 | — | 24.7 | 98.6 |
| Others | Remainder | Remainder | Remainder | Remainder |

T = Trace

The data of Table II show that 2-chloromethyl-1,3-dioxolane was recovered with an assay of about 80 percent, whereas, the data of Table V (distillate fraction 3) show that this cyclic acetal was recovered with an assay of in excess of 98%. Moreover the product reported in Table II contained significantly more of the acyclic ester by-products than the product reported in Table V, fraction 3.

EXAMPLE 4

The chlorination vessel described in Example 1 was purged with nitrogen and then charged with 8.022 moles (690.6 grams) of vinyl acetate and 1230 milliliters of benzene. The resulting solution was cooled to less than −10° C. and stirred rapidly. Chlorine gas (8.19 moles, 581 grams) was added to the vessel in the absence of light in the manner described in Example 1 over about 2 hours. The temperature of the solution during chlorination was about 1°–4° C. Chlorine remaining in the tubing and trap after the addition thereof to the chlorination vessel was completed was purged into the reaction mixture using a slow stream of nitrogen. The chlorinated solution was divided into three aliquots. Each aliquot was added to a stirred solution of ethylene glycol in a 2-liter Erlenmeyer flask. The flasks were stirred overnight (about 16 hours) at room temperature (about 22° C.). The amount of the chlorinated solution and ethylene glycol used for each aliquot were as follows:

| Aliquot No. | 1 | 2 | 3 |
|---|---|---|---|
| Chlorinated Solution, grams | 842.7 | 769.5 | 726.9 |
| Ethylene Glycol, grams | 358.8 | 491.6 | 618.2 |
| Mole ratio EG/VA | 2.0 | 3.0 | 4.0 |

Each aliquot was dried by refluxing the benzene in a Dean-Stark apparatus for from 3 to 4 hours. The aqueous phase collected from aliquots 1, 2 and 3 amounted to 99.0, 101.8 and 103.2 grams respectively. The solutions remaining in the pot were one phase and were stirred at room temperature. Samples of each aliquot remaining in the pot were taken and analyzed by GC. Results are tabulated in Table VI.

TABLE VI

| | Peak Area % Aliquot | | |
|---|---|---|---|
| Component | 1 | 2 | 3 |
| Water | 0.7 | 0.5 | 0.2 |
| Chloroacetaldehyde | 3.6 | 0.7 | 0.5 |
| Benzene | 37.2 | 33.0 | 28.0 |
| 2-Chloroethanol | 8.4 | 12.9 | 13.5 |
| Ethylene Glycol | 1.0 | 6.8 | 16.9 |
| 2-Chloroethyl Acetate | 10.2 | 6.1 | 3.8 |
| 2-Hydroxyethyl Acetate | 6.2 | 13.0 | 14.3 |
| 2-Chloromethyl-1,3-Dioxolane | 25.3 | 23.4 | 20.2 |
| Ethylene Diacetate | 7.2 | 3.5 | 2.4 |
| Others | 0.2 | 0.2 | 0.1 |

1156.1, 1055.6 and 997.3 grams of 20 percent aqueous sodium hydroxide were added respectively to dried aliquots 1, 2 and 3 and stirred for 20 hours at room temperature. Each of the resulting mixtures was phase separated. Each aqueous phase was extracted with about 150 milliliters of benzene and the resulting benzene extract added to the parent separated organic phase. Amounts of each phase are tabulated in Table VII. Each of the combined organic phases was topped in a 1 inch×12 inch glass helice-packed distillation column to remove benzene. A single fraction of material boiling at less than 145° C. was removed. The material remaining in the still pot was recovered and analyzed by GC. The results are reported in Table VII.

TABLE VII

|  | 1 | 2 | 3 |
|---|---|---|---|
|  |  | Aliquot |  |
| Aqueous Phase Separated, grams | 1527.8 | 1544.9 | 1604.0 |
| Combined Organic Phase, grams | 809.8 | 770.6 | 740.8 |
| Benzene Toppings |  |  |  |
| Component |  | Peak Area % |  |
| Water | 0.2 | 0.9 | 0.4 |
| Chloroacetaldehyde | T | T | T |
| Benzene | 98.9 | 97.7 | 99.3 |
| 2-Chloromethyl-1,3-Dioxolane | 0.2 | 0.9 | 0.1 |
| Unknowns | 0.7 | 0.5 | 0.1 |
| Pot Residue |  |  |  |
| Component |  |  |  |
| Water | 0.2 | 0.1 | 0.2 |
| Chloroacetaldehyde | T | T | T |
| 2-Chloroethyl Acetate | 0.2 | 0.7 | 1.0 |
| 2-Chloromethyl-1,3-Dioxolane | 98.9 | 98.6 | 98.0 |
| Unknowns | 0.6 | 0.5 | 0.8 |

T = Trace

The data of Example 4 (Tables VI and VII) show that 2-chloromethyl-1,3-dioxolane of high assay can be prepared by alkaline hydrolysis of the reaction product of ethylene glycol with 1,2-dichloroethyl acetate.

While the present invention has been illustrated by the preparation of 2-chloromethyl-1,3-dioxolane, similar results are expected for the preparation of 2-halomethyl-1,3-dioxepane-, dioxolan-, and dioxane cyclic acetals, the halogen being selected from the group of chlorine and bromine, by use of the corresponding 1,2-dihaloethyl acetate and $C_2$–$C_4$ aliphatic diols.

Although the present process has been described with reference to specific details of certain embodiments thereof, it is not intended that such details should be regarded as limitations upon the scope of the invention except as and to the extent that they are included in the accompanying claims.

We claim:

1. In the process for producing 2-halomethyl-1,3-cyclic acetal wherein vinyl acetate is halogenated to produce a first reaction mixture containing 1,2-dihaloethyl acetate, said halogen being selected from the group consisting of chlorine and bromine, and 1,2-dihaloethyl acetate in the first reaction mixture is reacted with a $C_2$–$C_4$ aliphatic diol to produce a second reaction mixture containing 2-halomethyl-1,3-cyclic acetal and acyclic ester by-products, the improvement which comprises (a) contacting the second reaction mixture with an aqueous alkaline reagent which provides the strong nucleophilic groups, $OH^-$ in an amount and for a time sufficient to substantially hydrolyze the hydrolyzable acyclic ester by-products in said second reaction mixture, thereby forming an aqueous phase and an organic phase, (b) separating the said organic phase and the aqueous phase, and (c) heating the organic phase to remove the readily volatile components of the organic phase, thereby to produce 2-halomethyl-1,3-cyclic acetal of improved purity.

2. The process of claim 1 wherein the alkaline reagent is an alkali metal hydroxide.

3. The process of claim 2 wherein the alkali metal hydroxide is sodium hydroxide or potassium hydroxide.

4. The process of claim 3 wherein the alkaline hydrolysis is conducted for from about 2 to 20 hours at from 20° C. to 90° C.

5. The process of claim 3 wherein the alkaline hydrolysis is conducted at from about 50° C. to 90° C. for from about 2 to 4 hours.

6. The process of claim 3 wherein the mole ratio of alkali metal hydroxide to 1,2-dihaloethyl acetate varies from about 1.7:1 to about 2.3:1.

7. The process of claim 2 wherein the 2-halomethyl-1,3-cyclic acetal corresponds to the following graphic formula:

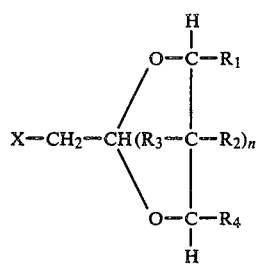

wherein X is chlorine or bromine, $R_1$, $R_2$, $R_3$ and $R_4$ are hydrogen or methyl, and n is an integer from 0 to 2.

8. In the process for producing 2-chloromethyl-1,3-dioxolane wherein vinyl acetate is chlorinated to produce a first reaction mixture containing 1,2-dichloroethyl acetate, and said first reaction mixture is admixed with ethylene glycol to form a second reaction mixture containing 2-chloromethyl-1,3-dioxolane and acyclic ester by-products including 2-chloroethyl acetate, the improvement which comprises:

(a) removing water from the second reaction mixture, (b) contacting the water-lean second reaction mixture with aqueous sodium hydroxide in amounts and for a time sufficient to substantially hydrolyze 2-chloroethyl acetate and other hydrolyzable acyclic ester by-products in the second reaction mixture, thereby to form an aqueous phase and an organic phase, (c) separating the aqueous phase and the organic phase, and (d) heating the organic phase to remove the readily volatile components of the organic phase, thereby to produce 2-chloromethyl-1,3-dioxolane of improved purity.

9. The process of claim 8 wherein the chlorination is conducted in an inert organic solvent.

10. The process of claim 9 wherein the solvent is benzene.

11. The process of claim 8 wherein an inert organc solvent which forms an azeotrope with water at least than about 85° C. is present in the second reaction mixture, and water is removed from the second reaction mixture by azeotropic distillation.

12. The process of claim 11 wherein the organic solvent is benzene, cyclohexane, ethylene dichloride, pentane or hexane.

13. The process of claim 11 wherein the alkaline hydrolysis is performed by refluxing the mixture of aqueous sodium hydroxide and the second reaction mixture until hydrolysis of the ester by-products is substantially complete.

14. The process of claim 11 wherein the alkaline hydrolysis is performed by stirring the mixture of aqueous sodium hydroxide and the second reaction mixture at ambient temperature for from 0.5 to 20 hours.

15. The process of claim 8 wherein the aqueous sodium hydroxide is an aqueous solution of from 5 to 35 weight percent sodium hydroxide.

16. The process of claim 11 wherein from 1.7 to 17 equivalents of sodium hydroxide, based on the amount of vinyl acetate chlorinated, are used in the alkaline hydrolysis step.

17. The process of claim 16 wherein the alkaline hydrolysis is conducted at from about 50° C. to 90° C. for from about 2 to 4 hours.

18. The process of claim 17 wherein the organic phase of step (d) is heated to temperatures sufficient to remove the organic solvent and organic components within that phase which are more volatile than 2-chloromethyl-1,3-dioxolane.

19. The process of claim 18 wherein the 2-chloromethyl-1,3-dioxolane product is at least 88 percent pure.

* * * * *

UNITED STATES PATENT AND TRADEMARK OFFICE
CERTIFICATE OF CORRECTION

PATENT NO. : 4,532,338
DATED : July 30, 1985
INVENTOR(S) : Steven E. Pamer and James A. Cook, Jr.

It is certified that error appears in the above-identified patent and that said Letters Patent are hereby corrected as shown below:

Claim 1 (a) line 3, "groups," should be --group,--

Claim 11, line 2, "least" should be --less--.

Signed and Sealed this

Twenty-ninth Day of October 1985

[SEAL]

Attest:

DONALD J. QUIGG

Attesting Officer

Commissioner of Patents and Trademarks—Designate